US006448053B1

(12) United States Patent
Lin et al.

(10) Patent No.: US 6,448,053 B1
(45) Date of Patent: *Sep. 10, 2002

(54) ERYTHRITOL-PRODUCING YEAST STRAINS

(75) Inventors: Shie-Jea Lin; Chiou-Yen Wen; Wen-Haw Hsu; Guey-Yuh Liou; Wen-Shen Chu, all of Hsinchu (TW)

(73) Assignee: Food Industry Research and Development Institute (TW)

( * ) Notice: Subject to any disclaimer, the term of this patent is extended or adjusted under 35 U.S.C. 154(b) by 0 days.

This patent is subject to a terminal disclaimer.

(21) Appl. No.: 09/962,908

(22) Filed: Sep. 25, 2001

Related U.S. Application Data

(63) Continuation of application No. 09/585,926, filed on Jun. 2, 2000, now Pat. No. 6,300,107.

(51) Int. Cl.⁷ .................................................. C12P 7/04
(52) U.S. Cl. ...................... 435/157; 435/158; 435/171; 435/911; 435/917
(58) Field of Search ............................... 435/158, 157, 435/171, 911, 917

(56) References Cited

U.S. PATENT DOCUMENTS 4,923,812 A * 5/1990 Horikita et al. ............. 435/158
4,939,091 A * 7/1990 Sasaki et al. ............... 435/158
5,902,739 A   5/1999 Abe et al.

FOREIGN PATENT DOCUMENTS

JP         9-154589         6/1997

OTHER PUBLICATIONS

Dooms et al., "Polyol Synthesis and Taxonomic Characters in the Genus", Antonie van Leeuwenhoek 37:107–118, 1971.

Yong Kum Park et al., "Biochemical Characteristics of Osmophilic Yeasts Isolated from Pollens and Honey", Biosci. Biotech. Biochem. 60(11), 1872–1873, 1996.

Hajny, G.J. et al. Erythritol production by a yeast–like fungus. Applied Microbiology, 12:240–246. May 1964.*

* cited by examiner

Primary Examiner—Christopher R. Tate
Assistant Examiner—Kailash C. Srivastava
(74) Attorney, Agent, or Firm—Fish & Richardson P.C.

(57) ABSTRACT

A method of producing erythritol. The method includes growing in a culture an isolated yeast strain that possesses certain unique characteristics and is capable of converting glucose to erythritol in a glucose-containing medium, and purifying erythritol from the culture.

25 Claims, No Drawings

ERYTHRITOL-PRODUCING YEAST STRAINS

CROSS REFERENCE TO RELATED APPLICATIONS

This application is a continuation and claims the benefit of priority under 35 USC § 120 of U.S. application Ser. No. 09/585,926, filed Jun. 2, 2000 is now 6,300,107, now allowed.

BACKGROUND OF THE INVENTION

Erythritol, a sugar alcohol, is 60–80% as sweet as sucrose. Yet, it has a calorific value only about one tenths that of sucrose and does not contribute to dental caries. Also, unlike many sugar alcohols, it does not cause diarrhea. Further, erythritol possesses excellent processing properties: It is heat-stable; and it does not react with amino groups and therefore does not cause browning of organic substance.

Erythritol can be found in lichen, hemp leaves, mushrooms, fermentative foods (e.g., wine and soy sauce), and microorganisms. Among erythritol-producing microorganisms are yeast strains of the Pichia, Candida, Torulopsis, Trigonopsis, Moniliella, Aureobasidium, and Trichosporon genera.

SUMMARY OF THE INVENTION

The present invention relates to new yeast strains which are capable of converting glucose into erythritol in a simple medium.

The yeast strains of this invention are characterized by an absence of motile spores or zoospore (i.e., spores having flagella); septate mycelia (i.e., mycelia having dividing walls); asexual reproduction (i.e., reproduction not involving kasogamy and meiosis); an absence of reniform cells; conidia optionally formed on short denticles (i.e., small tooth-like projections) but not on elongate stalks; an absence of ballistoconidia (i.e., forcibly discharged conidia); non-monopolar budding on a broad base (i.e., a multiplication process in which there is no development of a new cell from a single-pole outgrowth); acropetal chains of blastoconidia (i.e., conidia characterized by a marked enlargement of a recognizable conidial initial before the initial is delimited by a septum); dark brown, thick-walled chlamydospores (i.e., asexual 1-celled spores each originating endogenously and singly within part of a pre-existing cell by the contraction of the protoplast); a fermentative ability (i.e., an ability to ferment semi-anaerobically at least one carbon source); an ability to assimilate sucrose, glycerol and maltose; an inability to assimilate lactose; an inability to ferment galactose; an ability to grow in a vitamin-free medium; and an ability to grow at 25° C., 30° C., 35° C. and 36° C. Optionally, the yeast strains of this invention can be further characterized by an ability to ferment sucrose, glucose (i.e., D-glucose) or maltose; or an ability or inability to assimilate galactose.

The strains' ability or inability to ferment or assimilate a specific carbon source, to grow in a vitamin-free medium, and to grow at a specific temperature can be determined following the procedures described in the actual examples below.

Also contemplated within the scope of this invention are yeast strains characterized by the morphological traits set forth above and the physiological traits listed in Table 1, 2, 3, 4, 5 or 6 below. Examples include, but are not limited to, 6 strains deposited on Jan. 27, 2000 at the American Type Culture Collection, 10801 University Blvd., Manassas, Va. 20110–2209, USA. The accession numbers of the deposited strains are PTA-1227, PTA-1228, PTA-1229, PTA-1230, PTA-1231, and PTA-1232. Mutants derived from the deposited strains are also within the scope of this invention.

The yeast strains of the present invention are closest to *Moniliella acetobuten*. Indeed, their morphological traits as described above coincide with those of *M. acetobuten*. On the other hand, their physiological characteristics differ only slightly from *M. acetobuten*. For example, unlike *M. acetobuten*, the strains of this invention do not assimilate lactose. Further, they are capable of converting glucose to erythritol in a simple medium (e.g., glucose and yeast extract only) at a rate unexpectedly higher than *M. acetobuten*.

Other features or advantages of the present invention will be apparent from the following detailed description (including actual examples) and also from the appending claims.

DETAILED DESCRIPTION OF THE INVENTION

Yeast strains of the present invention can be isolated from natural sources, e.g., samples having high sugar contents such as honey, preserved fruit, and pollen. Each strain is identified based on its capability to convert glucose to erythritol and its various morphological and physiological traits. A yeast strain of this invention is capable of converting 1 g of glucose into at least 0.3 g of erythritol (i.e., conversion rate $\geq 30\%$). The conversion rate is determined by culturing the strain in a 10-ml broth containing 30% glucose and 1% yeast extract (initial cell density $1\times10^5$ cells/ml) in a 50 ml flask in a rotary shaker at 150 rpm and 30° C. for 6 days. The morphological traits are determined following growth on 4% malt extract/0.5% yeast extract agar for 10 days at 20° C. See, The Yeasts, A Taxonomic Study, Edited by Kurtzman et al., 4th Ed., page 785, Elsevier, Amsterdam (1998). The physiological traits, on the other hand, are determined by the methods described in the actual examples below.

Other yeast strains of this invention can be variants derived from strains isolated from natural sources. For example, such strains may be mutants obtained by UV irradiation, N-methyl-N'-nitrosoguanidine treatment, ethyl methanesulfonate treatment, nitrous acid treatment, acridine treatment, and the like. They also may be recombinant strains genetically produced by means of cell fusion or recombinant DNA techniques.

A skilled person in the art can obtain and utilize yeast strains of the present invention to the fullest extent based on the following specific examples, which are merely illustrative and not limitative of the remainder of the disclosure. All publications cited herein are incorporated by reference.

EXAMPLES 370 samples were collected from honey, raw pollen, processed pollen, preserved fruit, fresh fruit, waste water from sugar manufacture, and molasses. The collected samples were then cultured in a medium containing 40% glucose and 1% yeast extract for 3–4 days. The cultures were then spread on agar plates containing 20% glucose and 1% yeast extract and then incubated in the incubator at 30° C. for 3–4 days. Different strains were picked based on colony appearances, inoculated into a broth containing 30% glucose and 1% yeast extract, and cultured in an incubator at 30° C. for 4–5 days. The amount of erythritol in each supernatant was determined by HPLC and TLC so as to determine the erythritol-producing ability of the isolated strain.

HPLC analysis was performed by Hewlett Packard H4033A analyzer on an Ion-300 chromatography column, using 0.1 N sulfuric acid as the flowing phase with a flowing rate of 0.4 ml/min, the temperature being set at 75° C. For TLC analysis, the Neissner et al. procedure was followed. (Neissner, et al. 1980. Herstellung, aanalyse und DC-trennung von fettsaure erythritpartialestern. FETTE•SEIFEN•ANSTRICHMITTEL. 82:10-16.) After rinsing Kieselgel 60F254 (Merck) with 4% boric acid, the gel was heated in an incubator at 105° C. for 20 minutes before use. The spreading solvent was ethylmethylketone:acetone:water (100:10:10 by vol.) and the color developing agent was KMnO4 in conc. sulfuric acid.

Erythritol purified from a supernatant by HPLC or TLC was further purified by extraction and then dried under reduced pressure. The further purified product and an erythritol standard were acetylated according to the method of Shindou et al. (Shindou et al. 1989. Identification of erythritol by HPLC and GC-MS and quantitative measurement in pulps of various fruits. J. Agric. Food Chem. 37:1474–1476.) The resulting sample was assayed by GC-MS to determine if the re-purified product was identical to that of the standard sample.

A total of 630 strains were isolated from the 370 samples. Among them, 22 exhibited the ability to produce erythritol. 6 erythritol-producing strains were selected from 161 isolates from processed honey, processed pollen and molasses, and showed erythritol conversion rates between 0.5 to 1.5%. The low conversion rates may be due to elimination of erythritol-producing microorganisms, as the samples had been subjected to heating and drying before they were collected. 3 strains, i.e., 440, 441 and 442, among 26 strains isolated from 49 honey samples (most of which were not processed) were found to produce erythritol from glucose at high conversion rates (>30%). Among 66 strains isolated from waste water and mud samples from sugar factories, none of them showed the capability to produce erythritol. 3 good erythritol-producing strains (conversion rates >30%), i.e., 166-2, 262-1 and 278-3, were isolated from raw pollen and preserved fruit samples.

To study the effect of glucose concentration on erythritol production, strains 166-2, 262-1 and 278-3 were each cultured in media containing 1% yeast extract and 20%, 30% and 40% glucose, respectively, in a rotary shaker at 150 rpm and 30° C. for 1–6 days (10 ml medium in a 50 ml flask; initial cell density $1 \times 10^5$ cells/ml). The amounts of erythritol produced were then determined. The results show that the three strains grown in 30% glucose media for 6 days (the standard procedure for determining the conversion rate of a yeast strain of this invention), all showed conversion rates exceeding 30%. Moreover, after culturing in a medium containing 40% glucose for 6 days, the conversion rates of all three strains were shown to be about 30%. As to consumption of glucose, when cultured in a medium containing 30% glucose, strain 166-2 consumed all glucose on day 5 and strains 262-1 and 278-3 on day 6.

Increase in ionic osmotic pressure was found to lower the conversion rates for all 3 strains as shown by a study in which KCl or NaCl, at 0.5, 1.0 and 1.5 M, respectively, was added to 30% glucose media. A pH profile study showed that at pH 4.0–7.0, the conversion rates of the 3 strains grown in 30% glucose media were about the same. The conversion rates decreased at pH 8. Strains 166-2, 262-1 and 278-3 were also cultured in 30% media at 25° C., 30° C., and 35° C., respectively. All 3 strains showed the highest conversion rates at 30° C. and the lowest at 25° C.

The effects of different media on the production of erythritol were also studied. No erythritol was produced by all three strains when 30% glucose was replaced with 30% maltose. Replacement of 30% glucose with 30% maltodextrin or replacement of 1% yeast extract with 6% corn steep liquor or 6% soybean flour resulted in significant decrease of conversion rates. In addition, the effects of different concentrations of yeast extract, 0.5%, 0.75% and 1.0%, in media were investigated. The results showed that the conversion rates increased in proportion to the level of yeast extract. Further, the conversion rates were not significantly affected by the addition of various minerals at different concentrations, i.e., $MgSO_4 \cdot 7H_2O$ (0.02% to 0.1%), $KH_2PO_4$ (0.001% to 0.02%), $CaCl_2 \cdot 2H_2O$ (0.1% to 0.4%), and $CaCO_3$ (0.1% to 1%).

In addition to culturing in flasks as described above, each of strains 166-2, 262-1, and 278-3 was also cultured in a 5-liter fermentor containing a 2-liter 30% glucose/1% yeast extract medium at 30° C. for 6–7 days (rotation: 150 rpm; aeration: 1 vvm or volume/minute/medium volume; initial cell density: $1 \times 10^5$ cells/ml). The conversion of glucose to erythritol was about completed by both strains 166-2 and 262.1 at the end of day 5. Strain 278-3 converted glucose to erythritol at a slower rate and the conversion was not completed until day 7.

On day 7, the supernatant from each culture was collected by centrifugation, decolorized with active carbon, and then passed through ion exchange resins (IRA-410:IRA-120B= 2:1) to remove impurities. After condensation by evaporation and recrystallization, erythritol was obtained as a clear white crystal. The structure of the resulting erythritol crystal was confirmed by 1H and 13C NMR.

Strains 166-2, 262-1, 278-3, 440, 441 and 442 were found to be capable of producing 98.7, 104.1, 117, 99, 97.8 and 102.6 g of erythritol per liter, respectively, when they were each culitvated in 10 ml of 30% glucose/1% yeast extract medium (initial cell density $1 \times 10^5$ cells/ml) in a 50 ml flask in a rotary shaker at 150 rpm and 30° C. for 6 days.

The physiological traits of strains 166-2, 262-1, 278-3, 440, 441 and 442 were determined following the procedures provided in The Yeasts, A Taxonomic Study, Edited by Kreger-van Rij et al., 3rd Ed., pages 76–101, Elsevier, Amsterdam (1984).

In particular, the fermentation of all sugars was tested in 2% (w/v) solutions in Durham tubes, the inocula were from 48-hour malt extract agar cultures, and after inoculation the cells were incubated in fermentation basal medium at 25° C. See pages 78–79.

The tests on aerobic utilization (assimilation) of carbon compounds were conducted following a method set forth at pages 81–83 under the subheading "1. Liquid medium assimilation tests." More specifically, cell suspensions were made up with sterile tap water, and after inoculation the cells were incubated at 25° C. A 10-fold concentrated medium was prepared by dissolving 6.7 g of Bacto yeast nitrogen base and the appropriate amount of the carbon compound equivalent to glucose (i.e., containing the same amount of carbon as 5 g glucose) in 100 ml demineralized water. For simplicity, all positive reactions (i.e., 1+, 2+ and 3+) are indicated as "+".

The tests on aerobic utilization (assimilation) of nitrogen compounds were conducted following a method set forth at pages 85–86 under the subheading "1. Assimilation in liquid medium." For simplicity, all positive reactions (i.e., 1+, 2+ and 3+) are indicated as "+".

The tests on growth in vitamin-free media were conducted following a method set forth at pages 86–87 under the subheading "3. Growth in vitamin-free medium, vitamin requirements." For simplicity, all positive reactions (i.e., 1+, 2+ and 3+) are indicated as "+".

The tests on growth at various temperatures were conducted following a method set forth at pages 88–89 under the subheading "5. Growth at 37° C. and at other temperatures; maximum temperature of growth." Solid medium was used.

All of the test results are shown in Tables 1–6 below:

TABLE 1

Physiologial Characteristics of Strain 166-2

Semi-anaerobic fermentation:

| | | | |
|---|---|---|---|
| D-Glucose | + | D-Galactose | – |
| Maltose | + | Sucrose | + |
| Lactose | – | | |

Aerobic utilization and growth:

| | | | |
|---|---|---|---|
| D-Glucose | + | α,α-Trehalose | – |
| Sorbose | – | Cellobiose | + |
| D-Ribose | + | Arbutin | + |
| L-Arabinose | w | Lactose | – |
| D-Rhamose | – | Melezitose | – |
| Maltose | + | Starch | – |
| Methyl α-D-glucoside | – | Erythritol | + |
| Salicin | – | Xylitol | – |
| Melibiose | – | D-Glucitol | – |
| Raffinose | – | Galactitol | – |
| Inulin | – | D-Glucono-1,5-lactone | + |
| Glycerol | + | D-Gluconate | – |
| Ribitol | – | DL-Lactate | – |
| L-Arabinitol | – | Citrate | – |
| D-Mannitol | + | Enthanol | + |
| myo-Inositol | – | Butane | – |
| 2-keto-gluconate | – | Saccharate | – |
| Galacturonate | – | Nitrate | + |
| Succinate | + | Ethylamine | – |
| Methanol | – | Cadaverine | + |
| Propane | – | Creatinine | – |
| Quinate | – | Imidazole | – |
| Galactonate | – | Nitrite | + |
| D-Galactose | + | Lysine | + |
| Glucosamine | – | Creatine | – |
| Xylose | – | Glucosamine | – |
| D-Arabinose | w | | |
| Sucrose | + | | |

Growth Temperature:

| | | | |
|---|---|---|---|
| 25° C. | + | 30° C. | + |
| 35° C. | + | 36° C. | + |

TABLE 2

Physiologial Characteristics of Strain 262-1

Semi-anaerobic fermentation:

| | | | |
|---|---|---|---|
| D-Glucose | + | D-Galactose | – |
| Maltose | + | Sucrose | + |
| Lactose | – | | |

Aerobic utilization and growth:

| | | | |
|---|---|---|---|
| D-Glucose | + | α,α-Trehalose | – |
| Sorbose | – | Cellobiose | + |
| D-Ribose | + | Arbutin | + |
| L-Arabinose | w | Lactose | – |
| D-Rhamose | – | Melezitose | – |
| Maltose | + | Starch | – |
| Methyl α-D-glucoside | – | Erythritol | + |
| Salicin | – | Xylitol | – |
| Melibiose | – | D-Glucitol | – |

TABLE 2-continued

Physiologial Characteristics of Strain 262-1

| | | | |
|---|---|---|---|
| Raffinose | – | Galactitol | – |
| Inulin | – | D-Glucono-1,5-lactone | + |
| Glycerol | + | D-Gluconate | – |
| Ribitol | – | DL-Lactate | – |
| L-Arabinitol | – | Citrate | – |
| D-Mannitol | + | Enthanol | + |
| myo-Inositol | – | Butane | – |
| 2-keto-gluconate | – | Saccharate | – |
| Galacturonate | – | Nitrate | + |
| Succinate | + | Ethylamine | w |
| Methanol | – | Cadaverine | + |
| Propane | – | Creatinine | – |
| Quinate | – | Imidazole | – |
| Galactonate | – | Nitrite | + |
| D-Galactose | – | Lysine | + |
| Glucosamine | – | Creatine | – |
| Xylose | – | Glucosamine | – |
| D-Arabinose | – | | |
| Sucrose | + | | |

Growth Temperature:

| | | | |
|---|---|---|---|
| 25° C. | + | 30° C. | + |
| 35° C. | + | 36° C. | + |

TABLE 3

Physiologial Characteristics of Strain 278-3

Semi-anaerobic fermentation:

| | | | |
|---|---|---|---|
| D-Glucose | + | D-Galactose | – |
| Maltose | + | Sucrose | + |
| Lactose | – | | |

Aerobic utilization and growth:

| | | | |
|---|---|---|---|
| D-Glucose | + | α,α-Trehalose | – |
| Sorbose | – | Cellobiose | + |
| D-Ribose | – | Arbutin | + |
| L-Arabinose | – | Lactose | – |
| D-Rhamose | – | Melezitose | – |
| Maltose | + | Starch | – |
| Methyl α-D-glucoside | – | Erythritol | + |
| Salicin | – | Xylitol | – |
| Melibiose | – | D-Glucitol | – |
| Raffinose | – | Galactitol | – |
| Inulin | – | D-Glucono-1,5-lactone | + |
| Glycerol | + | D-Gluconate | – |
| Ribitol | – | DL-Lactate | – |
| L-Arabinitol | – | Citrate | – |
| D-Mannitol | + | Enthanol | + |
| myo-Inositol | – | Butane | – |
| 2-keto-gluconate | – | Saccharate | – |
| Galacturonate | – | Nitrate | + |
| Succinate | + | Ethylamine | – |
| Methanol | – | Cadaverine | + |
| Propane | – | Creatinine | – |
| Quinate | – | Imidazole | – |
| Galactonate | – | Nitrite | + |
| D-Galactose | – | Lysine | + |
| Glucosamine | – | Creatine | w |
| Xylose | – | Glucosamine | – |
| D-Arabinose | – | | |
| Sucrose | + | | |

Growth Temperature:

| | | | |
|---|---|---|---|
| 25° C. | + | 30° C. | + |
| 35° C. | + | 36° C. | + |

TABLE 4

Physiological Characteristics of Strain 440

Semi-anaerobic fermentation:

| | | | |
|---|---|---|---|
| D-Glucose | + | D-Galactose | − |
| Maltose | + | Sucrose | + |
| Lactose | − | | |

Aerobic utilization and growth:

| | | | |
|---|---|---|---|
| D-Glucose | + | D-Mannitol | + |
| D-Galactose | + | Galactitol | − |
| Sorbose | + | myo-Inositol | − |
| D-Glucosamine | − | D-Glucono-1,5-lactone | + |
| D-Ribose | + | D-Gluconate | − |
| L-Arabinose | − | D-Glucuronate | − |
| D Arabinose | − | D-Galacturonate | − |
| L-Rhamnose | − | Citrate | − |
| Sucrose | + | DL-Lactate | − |
| Maltose | + | Succinate | + |
| α,α-Trehalose | − | Methanol | − |
| Methyl α-D-glucoside | − | 2-keto-gluconate | − |
| Cellobiose | + | D-Xylose | − |
| Salicin | − | Ethanol | + |
| Arbutin | + | Propane | − |
| Melibiose | − | Saccharate | − |
| Lactose | − | Butane | − |
| Raffinose | − | Quinate | − |
| Melezitose | − | Galactonate | − |
| Inulin | − | Nitrate | + |
| Starch | − | Nitrite | + |
| Glycerol | + | Ethylamine | − |
| Erythritol | + | L-Lysine | + |
| Ribitol | − | Cadaverine | + |
| Xylitol | − | Vitamine-free growth | + |
| L-Arabinitol | − | With 0.01% (w/v) Cycloheximide | − |
| D-Glucitol | − | With 0.1% (w/v) Cycloheximide | − |

Growth Temperature:

| | | | |
|---|---|---|---|
| 25° C. | + | 30° C. | + |
| 35° C. | + | 36° C. | + |

TABLE 5

Physiological Characteristics of Strain 441

Semi-anaerobic fermentation:

| | | | |
|---|---|---|---|
| D-Glucose | − | D-Galactose | − |
| Maltose | − | Sucrose | − |
| Lactose | − | | |

Aerobic utilization and growth:

| | | | |
|---|---|---|---|
| D-Glucose | + | D-Mannitol | + |
| D-Galactose | − | Galactitol | − |
| Sorbose | + | myo-Inositol | − |
| D-Glucosamine | − | D-Glucono-1,5-lactone | + |
| D-Ribose | + | D-Gluconate | w |
| L-Arabinose | − | D-Glucuronate | − |
| D Arabinose | − | D-Galacturonate | − |
| L-Rhamnose | − | Citrate | − |
| Sucrose | + | DL-Lactate | − |
| Maltose | + | Succinate | + |
| α,α-Trehalose | − | Methanol | − |
| Methyl α-D-glucoside | − | 2-keto-gluconate | − |
| Cellobiose | + | D-Xylose | − |
| Salicin | − | Ethanol | + |
| Arbutin | + | Propane | − |
| Melibiose | − | Saccharate | − |
| Lactose | − | Butane | − |
| Raffinose | − | Quinate | − |
| Melezitose | − | Galactonate | − |
| Inulin | − | Nitrate | + |
| Starch | − | Nitrite | + |
| Glycerol | + | Ethylamine | − |
| Erythritol | + | L-Lysine | + |
| Ribitol | − | Cadaverine | + |
| Xylitol | − | Vitamine-free growth | + |
| L-Arabinitol | − | With 0.01% (w/v) Cycloheximide | − |
| D-Glucitol | − | With 0.1% (w/v) Cycloheximide | − |

Growth Temperature:

| | | | |
|---|---|---|---|
| 25° C. | + | 30° C. | + |
| 35° C. | + | 36° C. | + |

TABLE 6

Physiological Characteristics of Strain 442

Semi-anaerobic fermentation:

| | | | |
|---|---|---|---|
| D-Glucose | + | D-Galactose | − |
| Maltose | + | Sucrose | + |
| Lactose | − | | |

Aerobic utilization and growth:

| | | | |
|---|---|---|---|
| D-Glucose | + | D-Mannitol | + |
| D-Galactose | − | Galactitol | − |
| Sorbose | + | myo-Inositol | − |
| D-Glucosamine | − | D-Glucono-1,5-lactone | + |
| D-Ribose | + | D-Gluconate | − |
| L-Arabinose | − | D-Glucuronate | − |
| D Arabinose | − | D-Galacturonate | − |
| L-Rhamnose | − | Citrate | w |
| Sucrose | + | DL-Lactate | − |
| Maltose | + | Succinate | + |
| α,α-Trehalose | − | Methanol | − |
| Methyl α-D-glucoside | − | 2-keto-gluconate | − |
| Cellobiose | + | D-Xylose | − |
| Salicin | − | Ethanol | + |
| Arbutin | + | Propane | − |
| Melibiose | − | Saccharate | − |
| Lactose | − | Butane | − |
| Raffinose | + | Quinate | − |
| Melezitose | − | Galactonate | − |
| Inulin | − | Nitrate | + |
| Starch | − | Nitrite | + |
| Glycerol | + | Ethylamine | − |
| Erythritol | + | L-Lysine | + |
| Ribitol | − | Cadaverine | + |
| Xylitol | − | Vitamine-free growth | + |
| L-Arabinitol | − | With 0.01% (w/v) Cycloheximide | − |
| D-Glucitol | − | With 0.1% (w/v) Cycloheximide | − |

Growth Temperature:

| | | | |
|---|---|---|---|
| 25° C. | + | 30° C. | + |
| 35° C. | + | 36° C. | + |

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. For example, while all tested yeast strains are capable of growing in a medium containing 30% glucose and 1% yeast extract, those strains which can grow in such a medium only if it is supplemented with one or more nutrients are also contemplated within the scope of this invention. Thus, other embodiments are also within the claims.

What is claimed is:

1. A method of producing erythritol, the method comprising:
   growing in a culture an isolated yeast strain capable of converting glucose to erythritol in a medium containing 30% glucose and 1% yeast extract, said strain having the characteristics of:
   an absence of motile spores;
   septate mycelia;
   asexual reproduction;
   an absence of reniform cells;
   conidia optionally formed on short denticles but not on elongate stalks;
   an absence of ballistoconidia;
   non-monopolar budding on a broad base;
   acropetal chains of blastoconidia;
   dark brown, thick-walled chlamydospores;
   a fermentative ability;
   an ability to assimilate sucrose;
   an ability to assimilate glycerol;
   an ability to assimilate maltose;
   an inability to assimilate lactose;
   an inability to ferment galactose; and
   an ability to grow at 25° C.–36° C.; and
   purifying erythritol from the culture.

2. The method of claim 1, wherein the yeast strain further has the characterstic of an ability to ferment sucrose and an inability to assimilate galactose.

3. The method of claim 2, wherein the yeast strain further has the characteristic of an ability to ferment glucose and maltose.

4. The method of claim 1, wherein the yeast strain further has the characteristic of an ability to ferment sucrose and an ability to assimilate galactose.

5. The method of claim 4, wherein the yeast strain further has the characteristic of an ability to ferment glucose and maltose.

6. A method of producing erythritol, the method comprising:
   growing in a culture an isolated yeast strain capable of converting glucose to erythritol in a medium containing 30% glucose and 1% yeast extract, said strain having the characteristics of:
   an absence of motile spores;
   septate mycelia;
   asexual reproduction;
   an absence of reniform cells;
   conidia optionally formed on short denticles but not on elongate stalks;
   an absence of ballistoconidia;
   non-monopolar budding on a broad base;
   acropetal chains of blastoconidia;
   dark brown, thick-walled chlamydospores; and the physiological traits listed in one of Tables 1–6 of the specification; and
   purifying erythritol from the culture.

7. The method of claim 6, wherein the yeast strain has the characteristics of the physiological traits listed in Table 1 of the specification.

8. The method of claim 6, wherein the yeast strain has the characteristics of the physiological traits listed in Table 2 of the specification.

9. The method of claim 6, wherein the yeast strain has the characteristics of the physiological traits listed in Table 3 of the specification.

10. The method of claim 6, wherein the yeast strain has the characteristics of the physiological traits listed in Table 4 of the specification.

11. The method of claim 6, wherein the yeast strain has the characteristics of the physiological traits listed in Table 5 of the specification.

12. The method of claim 6, wherein the yeast strain has the characteristics of the physiological traits listed in Table 6 of the specification.

13. The method of claim 6, wherein the yeast strain is assigned by the American Type Culture Collection the accession number of PTA-1227, PTA-1228, PTA-1229, PTA-1230, PTA- 1231, or PTA-1232; or a mutant derived therefrom.

14. The method of claim 13, wherein the yeast strain is assigned the acession number PTA-1227.

15. The method of claim 13, wherein the yeast strain is assigned the accession number PTA-1228.

16. The method of claim 13, wherein the yeast strain is assigned the accession number PTA-1229.

17. The method of claim 13, wherein the yeast strain is assigned the accession number PTA-1230.

18. The method of claim 13, wherein the yeast strain is assigned the accession number PTA-1231.

19. The method of claim 13, wherein the yeast strain is assigned the accession number PTA-1232.

20. The method of claim 13, wherein the yeast strain is a mutant derived from the strain assigned the accession number PTA-1227.

21. The method of claim 13, wherein the yeast strain is a mutant derived from the strain assigned the accession number PTA-1228.

22. The method of claim 13, wherein the yeast strain is a mutant derived from the strain assigned the accession number PTA-1229.

23. The method of claim 13, wherein the yeast strain is a mutant derived from the strain assigned the accession number PTA-1230.

24. The method of claim 13, wherein the yeast strain is a mutant derived from the strain assigned the accession number PTA-1231.

25. The method of claim 13, wherein the yeast strain is a mutant derived from the strain assigned the accession number PTA-1232.

* * * * *